(12) United States Patent
Gogarnoiu

(10) Patent No.: US 7,618,258 B2
(45) Date of Patent: Nov. 17, 2009

(54) SLANTED DENTAL IMPLANT

(75) Inventor: Dumitru Gogarnoiu, Wynnewood, PA (US)

(73) Assignee: Form and Function Dental Services, P.C., Wynnewood, PA (US)

( * ) Notice: Subject to any disclaimer, the term of this patent is extended or adjusted under 35 U.S.C. 154(b) by 408 days.

(21) Appl. No.: 11/282,929

(22) Filed: Nov. 18, 2005

(65) Prior Publication Data

US 2006/0252009 A1 Nov. 9, 2006

(51) Int. Cl.
*A61C 8/00* (2006.01)
(52) U.S. Cl. .................................... 433/173
(58) Field of Classification Search .......... 433/172–176
See application file for complete search history.

(56) References Cited

U.S. PATENT DOCUMENTS

| | | | |
|---|---|---|---|
| 4,722,688 A | 2/1988 | Lonca | |
| 5,030,095 A | 7/1991 | Niznick | |
| 5,174,755 A * | 12/1992 | Fukuda | 433/173 |
| 5,549,690 A * | 8/1996 | Hollister et al. | 623/21.15 |
| 5,571,015 A | 11/1996 | Siegmund | |
| 5,577,912 A | 11/1996 | Prins | |
| 5,683,466 A * | 11/1997 | Vitale | 623/21.15 |
| 5,839,898 A | 11/1998 | Fernandes | |
| 5,863,200 A | 1/1999 | Hamada et al. | |
| 5,997,299 A | 12/1999 | Unger | |
| 6,164,969 A * | 12/2000 | Dinkelacker | 433/173 |
| 6,227,859 B1 | 5/2001 | Sutter | |
| 6,244,867 B1 | 6/2001 | Aravena et al. | |
| 6,273,721 B1 | 8/2001 | Valen | |
| 6,500,003 B2 | 12/2002 | Nichinonni | |
| D490,901 S | 6/2004 | Schulter et al. | |
| 6,788,986 B1 | 9/2004 | Traber et al. | |
| 6,814,577 B2 | 11/2004 | Blacklock | |
| 6,843,653 B2 | 1/2005 | Carlton | |
| 6,854,972 B1 * | 2/2005 | Elian | 433/173 |
| 2003/0031982 A1 | 2/2003 | Abarno | |
| 2003/0143514 A1 | 7/2003 | Peltier | |
| 2004/0018470 A1 | 1/2004 | Fernendes et al. | |
| 2004/0029075 A1 | 2/2004 | Peltier et al. | |
| 2004/0185418 A1 * | 9/2004 | Schulter et al. | 433/173 |

(Continued)

FOREIGN PATENT DOCUMENTS

EP     1 013 236 A1    6/2000

(Continued)

OTHER PUBLICATIONS

"Use of Site-Specific Anatomic Implants to Replace Missing Teeth," Fereidoun Daftary, Practical Procedures & Aesthetic Dentistry, Nov./Dec. 2005, vol. 17 No. 10, 4 pgs. Submitted for disclosure purposes only. Not admitted as prior art.

(Continued)

*Primary Examiner*—John J Wilson
(74) *Attorney, Agent, or Firm*—RatnerPrestia

(57) ABSTRACT

A dental implant fixture is disclosed. The implant fixture includes an elongated body extending along a longitudinal axis. The body has a first end and a second end. The first end includes a top face having a first portion having a first angle extending obliquely with respect to the longitudinal axis and a second portion having a second angle extending obliquely to the longitudinal axis and at an angle relative to the first portion.

15 Claims, 4 Drawing Sheets

U.S. PATENT DOCUMENTS

| | | |
|---|---|---|
| 2004/0185420 A1 | 9/2004 | Schulter et al. |
| 2005/0019730 A1 | 1/2005 | Gittleman |
| 2005/0084821 A1 | 4/2005 | Sims et al. |
| 2005/0136378 A1 | 6/2005 | Ennajimi et al. |
| 2005/0164146 A1 | 7/2005 | Cantor |

FOREIGN PATENT DOCUMENTS

| | | | |
|---|---|---|---|
| WO | WO 01/50972 | A2 | 7/2001 |
| WO | WO 03/047455 | A1 | 6/2003 |

OTHER PUBLICATIONS

"A Concept for a Biologically Derived, Parabolic Implant Design," Robert L. Holt et al., The International Journal of Periodontics & Restorative Dentistry, 2002, vol. 22 No. 5, pp. 473-481.

"Nobel Perfect™ Esthetic Scalloped Implant: Rationale for a New Design," Peter S. Wöhrle, Clinical Implant Dentistry and Related Research, 2003, vol. 5 Supplement 1, pp. 64-73.

"Dentoalveolar Morphology: Evaluation of Natural Root Form Versus Cylindrical Implant Fixtures," Fereidoun Daftary, Practical Periodontics and Aesthetic Dentistry, May 1997, vol. 9 No. 4, pp. 469-478.

"Modeling and Characterization of the CEJ for Optimization of Esthetic Implant Design," German O. Gallucci et al., The International Journal of Periodontics & Restorative Dentistry, Feb. 2004, vol. 24 No. 1, pp. 19-29. un-numbered photo page.

www.nobelbiocare.com/global/en/DentalImplants/starting.htm, Nobel Biocare, Jul. 7, 2005. Submitted for disclosure purposes only. Not admitted as prior art.

www.cidemeeting.com/dental/dental_implants_nobel_biocare.htm, Jul. 7, 2005. Submitted for disclosure purposes only. Not admitted as prior art.

Growing Your Business With Implants, Nobel Biocare Services AG, 2005, 16 pages.

International Search Report for international application No. PCT/US2006/027891, dated Jan. 19, 2007.

* cited by examiner

SLANTED DENTAL IMPLANT

FIELD OF THE INVENTION

The present invention relates to a dental implant having a top face that is slanted in multiple planes relative to a longitudinal axis of the implant.

BACKGROUND OF THE INVENTION

Dental implants are used to anchor a mechanical fixture, such as a dental prosthesis, into living bone. The implant is embedded into the bone to provide a solid foundation for connecting the dental prosthesis. The implants and their respective dental prostheses serve numerous purposes, such as to assist the user with chewing, to provide a mating surface for an opposing tooth to prevent the loss of the opposing tooth, and to present an aesthetically pleasing appearance.

Prior to inserting the implant into the bone, the bone must be drilled to provide a recess for the insert to be implanted. Previously, implants were designed to be placed perpendicularly to the bone surface. The location of the implant in the user's mouth and the amount of mouth opening severely limit the ability to insert the head of the implant perpendicularly to the bone. Due to these limitations, most often, implants are inserted at an angle with respect to the bone surface. The angular insertion of an implant creates two problems: a) the mesial top portion of the implant is inserted too deeply into the bone, and, b) the distal top portion protrudes excessively from the bone. Furthermore, two problems arise at different stages of the treatment. The bone overgrows on the mesial aspect, thus requiring additional osseous surgery to remove excess bone. Later on, on the mesial aspect, the bone continues to resorb in order to accommodate biologic width. Biologic width is approximately 2 millimeters of connective tissue that wraps around a natural tooth or an implant and is constant. Violation of this area creates chronic inflammation and bone resorption.

To attempt to compensate for these problems, other prior art implants have been provided that disclose a top face that extends in a single plane oblique to a longitudinal axis of the implant. Such implants provide improved mechanical properties and anchorage but do not address biological fit, the implant exit and its relationship to the gum tissue. It would be beneficial to provide a dental implant having a top face with multiple slants. Slants on the mesiodistal aspect allow an angulated insertion of the top of the implant, having the top of the implant parallel to the bone surface and thus enabling a smooth development of biological width. The facial slant yields better aesthetic results due to the curved outline at the gum level.

SUMMARY OF THE INVENTION

Briefly, the present invention provides a dental implant fixture. The implant fixture includes an elongated body extending along a longitudinal axis. The body has a first end and a second end. The first end includes a top face having a first portion with a first angle extending obliquely with respect to the longitudinal axis and a second portion having a second angle extending obliquely to the longitudinal axis and at an angle relative to the first portion.

Additionally, the present invention provides an implant fixture comprising an elongated body extending along a longitudinal axis The body has a first end and a second end. The first end comprises a top face having a compound slant relative to the longitudinal axis.

Further, the present invention provides an implant fixture comprising an elongated body extending along a longitudinal axis. The body has a first end and a second end. The first end comprises a top face extending in a plurality of planes. Each of the plurality of planes extends obliquely relative to the longitudinal axis.

BRIEF DESCRIPTION OF THE DRAWINGS

The foregoing summary, as well as the following detailed description of desired embodiments of the invention, will be better understood when read in conjunction with the appended drawings, which are incorporated herein and constitute part of this specification. For the purposes of illustrating the invention, there are shown in the drawings embodiments that are presently desired. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Certain terminology is used herein for convenience only and is not to be taken as a limitation on the present invention. The terminology includes the words specifically mentioned, derivatives thereof and words of similar import. The term "facial" is defined to mean a direction closer to the lips and cheek of the user. The term "lingual" is defined to mean a direction closer to the tongue of the user. The term "mesial" is defined to mean a direction closer to an imaginary centerline of the mouth of the user. The term "distal" is defined to mean a direction farther from the imaginary centerline of the mouth. The term "occlusal" is defined to mean the top surface, such as the chewing surface, of a tooth. The following describes desired embodiments of the invention. However, it should be understood based on this disclosure, that the invention is not limited by the desired embodiments of the invention.

Referring generally to the figures, several embodiments of a dental implant according to the present invention are shown. Dental implants are used to provide an anchor in a mouth for a prosthetic tooth, also known as a crown.

Figure 1:
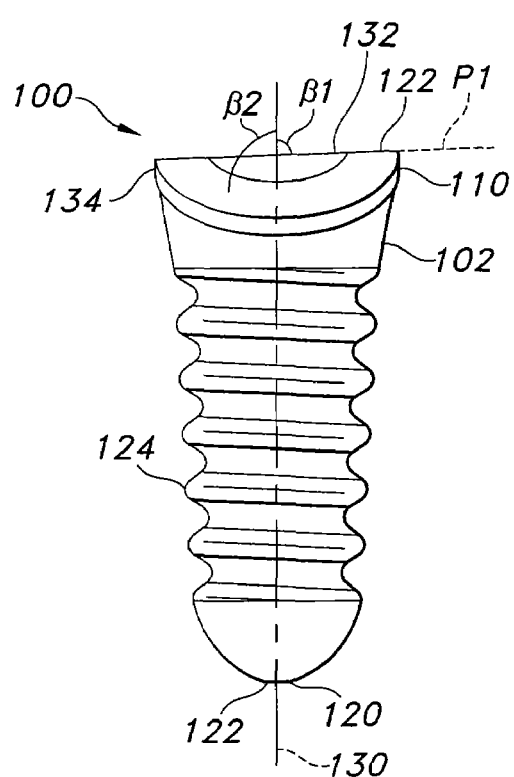
FIG. 1 is a facial side elevational view of a dental implant according to a first embodiment of the present invention.
Figure 2:
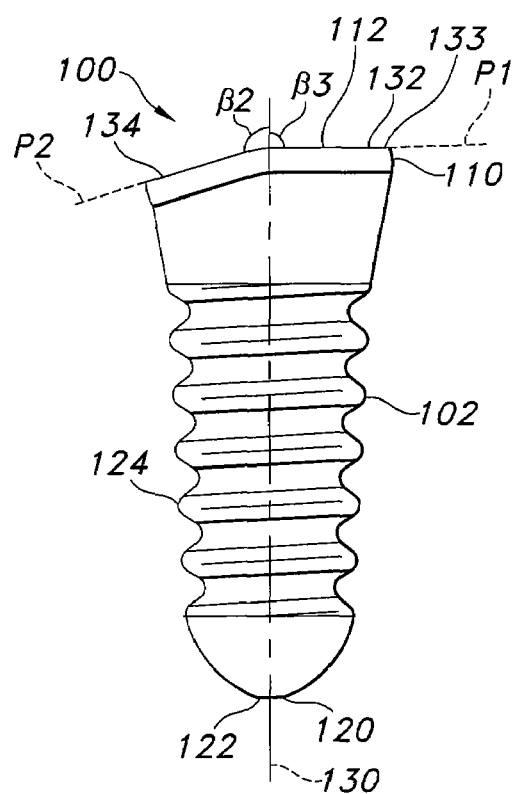
FIG. 2 is a mesial side elevational view of the dental implant shown in FIG. 1.
Figure 3:
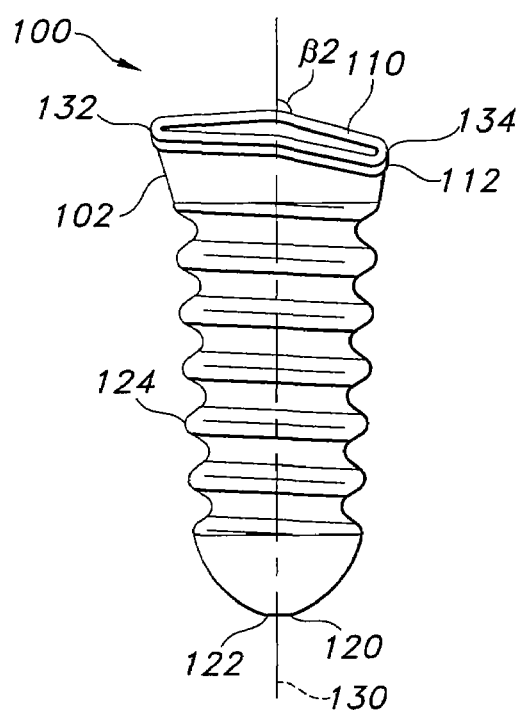
FIG. 3 is a distal side elevational view of the dental implant shown in FIG. 1.
Figure 4:
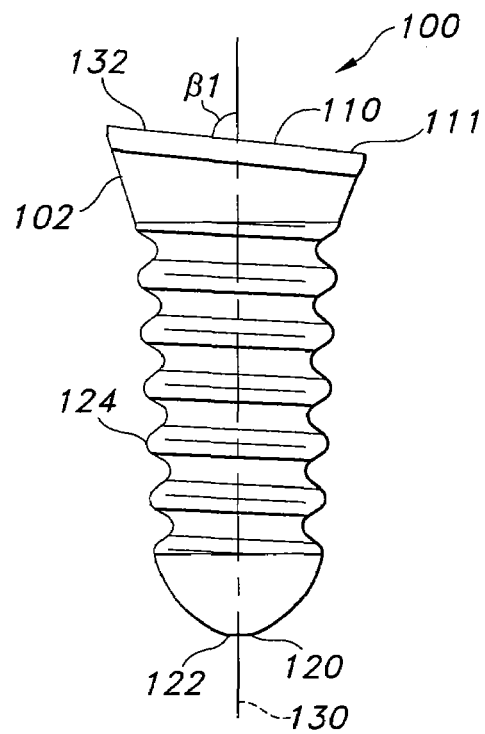
FIG. 4 is a lingual side elevational view of the dental implant shown in FIG. 1.
Figure 5:
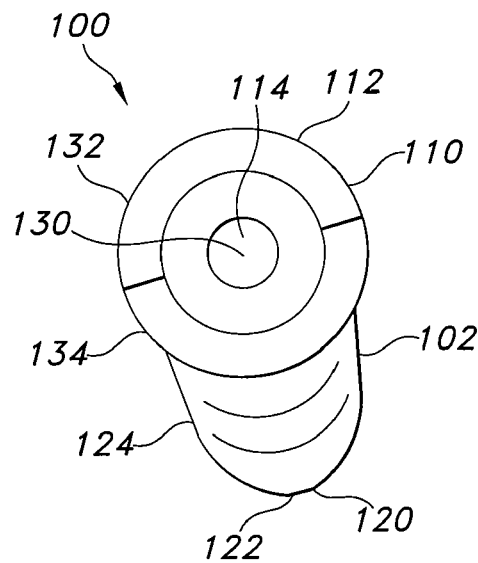
FIG. 5 is an occlusal view of the dental implant shown in FIG. 1.
Figure 6:
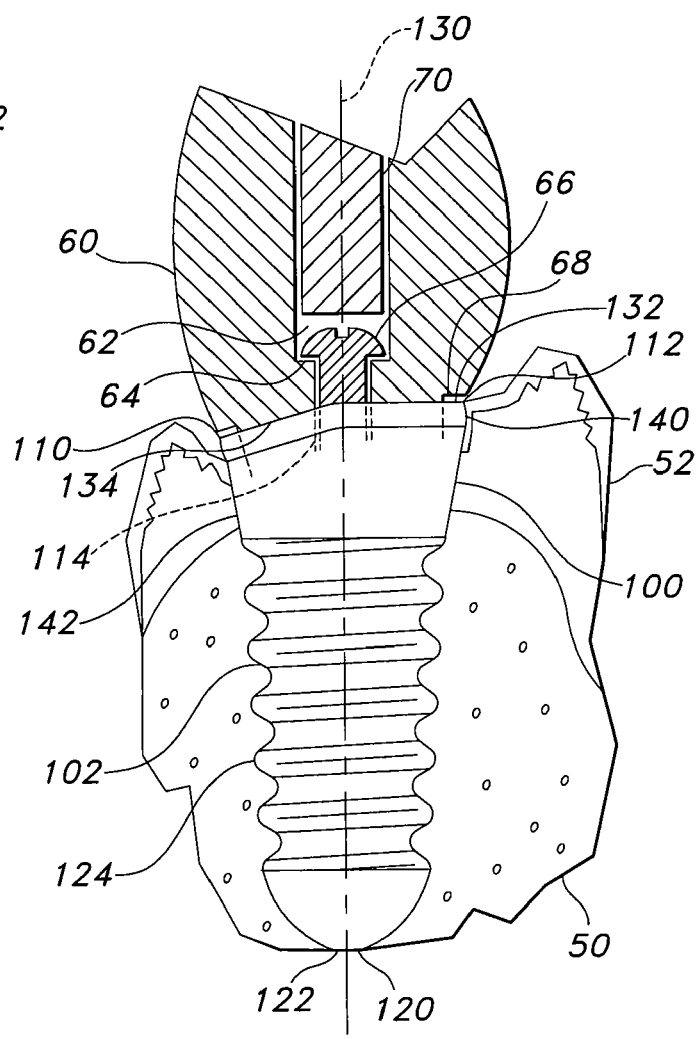
FIG. 6 is a mesial side view, partially in section, of the implant shown in FIG. 1 implanted into bone, with a dental prosthesis coupled to the implant.
Figure 8:
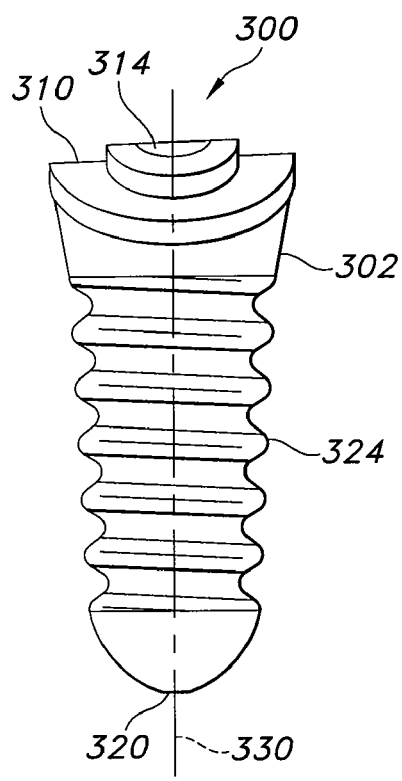
FIG. 8 is a facial side elevational view of a dental implant according to a third embodiment of the present invention.
Figure 9:
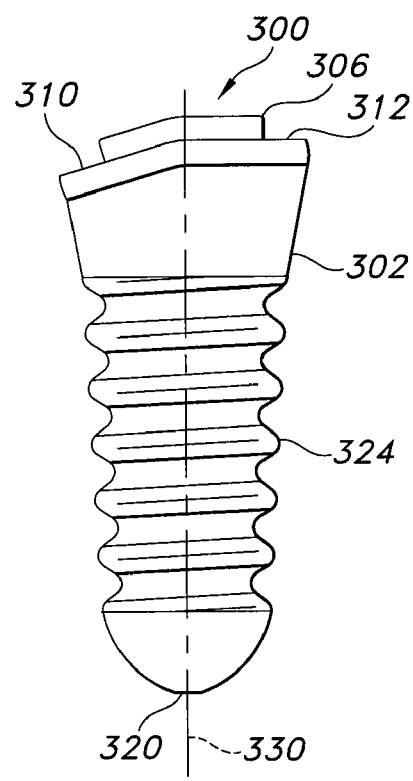
FIG. 9 is a mesial side elevational view of the dental implant shown in FIG. 8.
Figure 10:
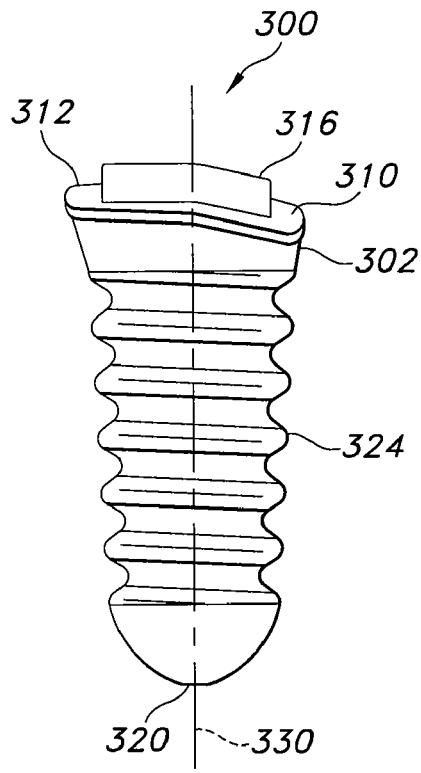
FIG. 10 is a distal side elevational view of the dental implant shown in FIG. 8.
Figure 11:
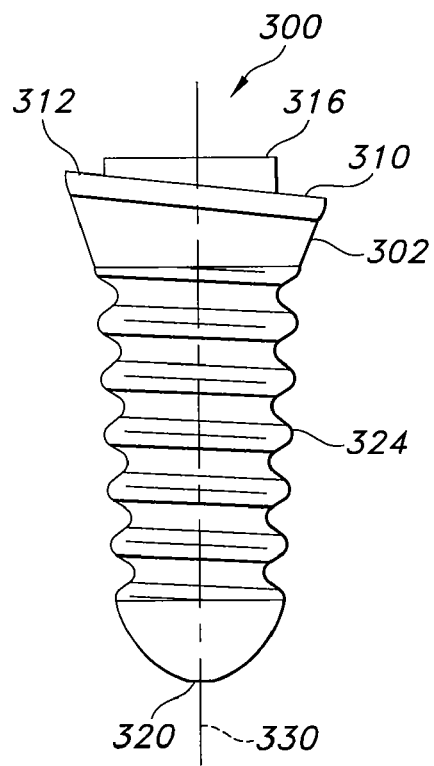
FIG. 11 is a lingual side elevational view of the dental implant shown in FIG. 8.

FIGS. 1-5 show five different views of an implant 100 according to a first embodiment of the present invention. FIG. 1 is a facial view; FIG. 2 is a mesial view; FIG. 3 is a distal view; FIG. 4 is a lingual view; and FIG. 5 is an occlusal view of implant 100. FIG. 6 shows a partial sectional view of the mesial view of implant 100 having been inserted into a bone 50, with a prosthetic tooth 60 connected to implant 100.

Referring to any of FIGS. 1-6, implant 100 includes a body 102 having a first end 110, a second end 120, and a longitudinal axis 130 extending between first end 110 and second end 120. First end 110 includes a top face 112. As seen in FIG. 5, desirably, top face 112 is generally annularly shaped with an opening 114 extending inward along longitudinal axis 130. Opening 114 provides a connection into which prosthetic tooth 60 is inserted.

Referring to FIGS. 1 and 4, top face 112 includes a first portion 132 that is slanted at a first angle β1 relative to longitudinal axis 130. Desirably, first portion 132 extends obliquely relative to longitudinal axis 130. First portion 132 forms a slanted mesiodistal face. Referring to FIGS. 1-3, top face 112 also includes a second portion 134 that is slanted at a second angle β2 relative to longitudinal axis 130. Second portion 134 forms a slanted facial face. Second portion 134 extends obliquely to longitudinal axis 130 and also at an angle to first portion 132. Second portion 134 may be slanted obliquely relative to first portion 132, or alternatively, second portion 134 may extend perpendicularly to first portion 132. Both slanted mesiodistal face and facial face may have angles β1, β2 that vary from shallow to steep, depending on the facial contours of the patient into which implant 100 is being inserted. Desirably, each angle β1, β2 extends between about 5 degrees and 45 degrees relative to longitudinal centerline 130, although those skilled in the art will recognize that angles β1, β2 may extend at different angles as well. Further, while first and second portions 132, 134 are depicted in FIGS. 2, 3, and 6 to extend approximately one half of top face 112, those skilled in the art will recognize that first and second portions 132, 134 may extend along different distances of top face 112.

Top face 112 also includes a third portion 133 that is slanted at a third angle ρ3 relative to longitudinal axis 130. Third portion 133 forms a lingual face. While third angle β3 is shown in FIG. 2 as extending approximately 90 degrees between lingual face and longitudinal axis 130, those skilled in the art will recognize that angle β3 may be more or less than 90 degrees.

With first and second portions 132, 134 slanting at different angles β1, β2, top face 112 can be said to have a compound slant relative to longitudinal axis 130. For implant 100 shown in FIGS. 1-5, the compound slant is a mesiodistal slant and a facial slant. Only a mesiodistal slant and a facial slant will satisfy the clinical requirements of both aesthetics and functionality for implant 100. These slants allow implant 100 to obtain perfect or near perfect alignment with the coronal part of the edentulous ridge of bone 50 after insertion.

Top face 112 is formed by a first plane P1 that extends along first portion 132 and out of the plane of FIG. 1 obliquely to longitudinal axis 130 along both a mesiodistal plane and also in a facial plane, and also a second plane P2 that extends along second portion 134 and out of the plane of FIG. 2 obliquely to longitudinal axis 130 along both the mesiodistal plane and also in a lingual plane. As can be seen from FIGS. 1 and 2, both planes P1, P2 extend obliquely relative to longitudinal axis 130. An intersection of planes P1 and P2 form a line that extends oblique to longitudinal axis 130.

Referring to FIG. 6, body 102 desirably includes a highly polished collar 140 that extends approximately 0.5 mm from first end 110 toward second end 120. Polished collar 140 allows the development of natural gingival sulcus around implant 100. A rougher surface 142 desirably extends approximately 1.5 mm below collar 140 toward second end 120. Rougher surface 142 accommodates biologic width of connective tissue 52 that typically surrounds a living tooth and provides a surface for connective tissue 52 to grow into after implant 100 is inserted into bone 50.

Referring to FIGS. 1-6, second end 120 is generally tapered from smaller to larger in a direction toward first end 110. Second end 120 is also closed with a rounded tip 122. Second end 120 also includes external threads 124 to form a threaded connection that may be used to secure implant 100 into bone 50, as shown in FIG. 6.

Referring now to FIG. 6 only, implant 100 is shown inserted into bone 50. Since implant 100 includes external threads 124, implant 100 may be screwed into bone 50 to provide a secure connection of implant 100 with bone 50.

After implant 100 is inserted into bone 50, crown 60 is secured to implant 100. Crown 60 includes a passage 62 extending longitudinally therethrough. A bottom part of passage 62 narrows, forming a lip 64. A coupling, such as a screw 66, is inserted through passage 62 and extends beyond crown 60 and into opening 114 for a threaded connection with mating threads (not shown) in opening 114. Screw 66 engages lip 64 to retain the head of screw 66 within passage 62. A bottom surface 68 of crown 60 is contoured to mate with top face 112 of implant 100 to provide a close fit between crown 60 and implant 100. After crown 60 is screwed onto implant 100, a filler 70 is inserted into passage 62 to cover screw 66.

Figure 7:
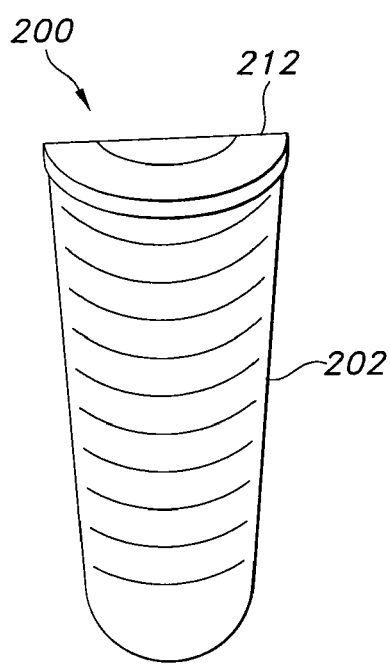
FIG. 7 is a facial side elevational view of a dental implant according to a second embodiment of the present invention.

While external threads 124 provide a desired connection between implant 100 and bone 50, those skilled in the art will recognize that external threads 124 may be omitted, as seen in implant 200 shown in FIG. 7. Implant 200 includes a rough surface body 202. Body 202 may be press-fit into bone and may optionally be secured to bone with an adhesive (not shown). A top face 212 desirably has the same compound slant as top face 112 described above.

Figure 12:
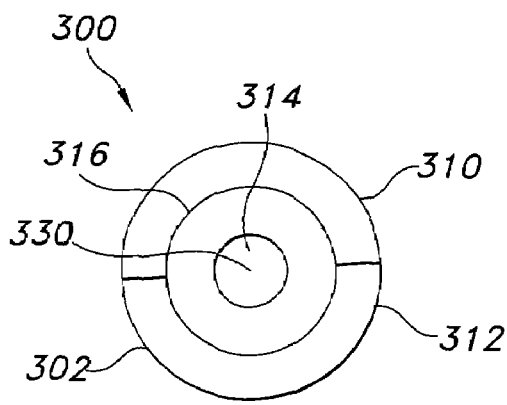
FIG. 12 is an occlusal view of the dental implant shown in FIG. 8.

Referring now to FIGS. 8-12, facial, mesial, distal, lingual, and occlusal views, respectively, of an alternate embodiment of an implant 300 are shown. Implant 300 includes a body 302 having a first end 310, a second end 320, and a longitudinal axis 330 extending between first end 310 and second end 320. First end 310 includes a top face 312. As seen in FIG. 12, desirably, top face 312 is generally annularly shaped with an opening 314 extending inward along longitudinal axis 330.

Figure 13:
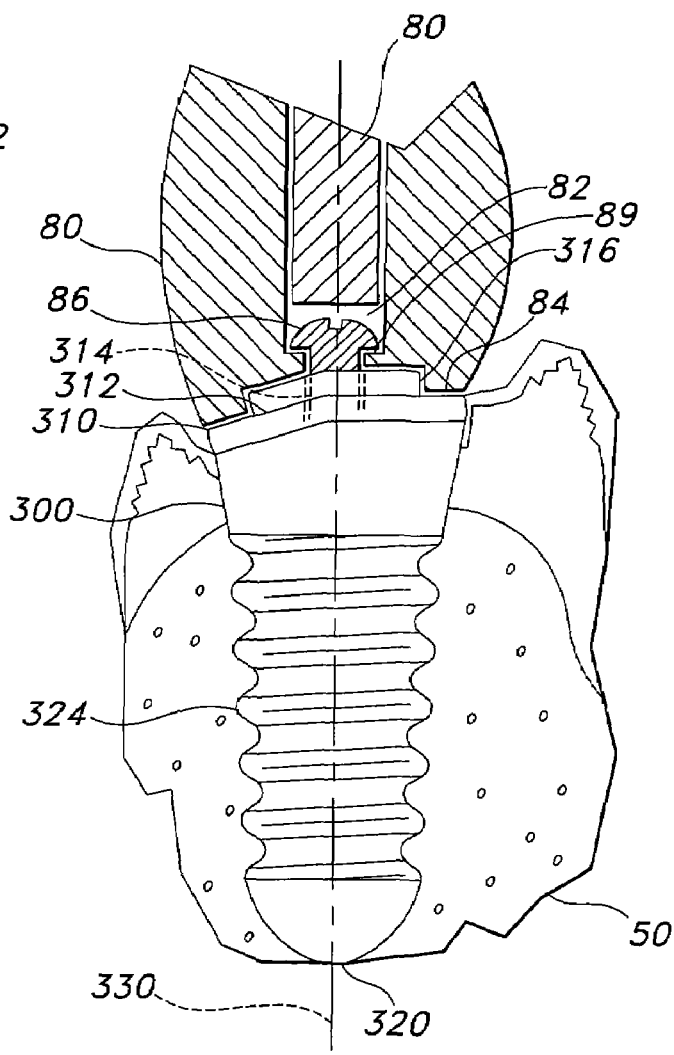
FIG. 13 is a mesial side view, partially in section, of the implant shown in FIG. 8 implanted into bone, with a dental prosthesis coupled to the implant.

An external connection 316 extends upward from top face 312, away from body 302. External connection 316 provides an alternate manner by which a crown 80, shown in FIG. 13, may be affixed to implant 300. Crown 80 includes a recess 82 that extends from the bottom of crown 80 upward. Recess 82 is sized to accept external connection 316 such that a bottom surface 84 of crown 80 rests on top face 312 of implant 300. Bottom surface 84 of crown 80 is contoured to mate with top face 312 to provide a close fit between crown 80 and implant 300.

After implant 300 is inserted into bone 50, crown 80 is secured to implant 300. Crown 80 includes a passage 82 extending longitudinally therethrough. A bottom part of passage 82 narrows, forming a lip 84. A coupling, such as a screw 86, is inserted through passage 82 and extends beyond crown 80 and into opening 314 for a threaded connection with mating threads (not shown) in opening 314. Screw 86 engages lip 84 to retain the head of screw 86 within passage 82. Bottom surface 84 of crown 80 is contoured to mate with top face 312 of implant 300 to provide a close fit between crown 80 and implant 300. After crown 80 is screwed onto implant 300, a filler 90 is inserted into passage 82 to cover screw 86.

Figure 14:
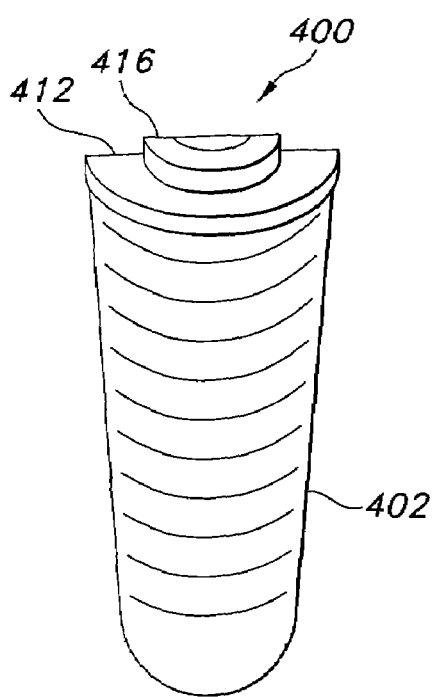
FIG. 14 is a facial side elevational view of a dental implant according to a fourth embodiment of the present invention.

Although implant 300 is shown in FIGS. 8-11 and 13 with threads 324, those skilled in the art will recognize that threads 324 may be omitted, such as in implant 400, shown in FIG. 14, which is similar to implant 200 shown in FIG. 7, having a rough surface body 402, but with an external connection 416 extending upward from a top face 412.

Desirably, implants 100, 200, 300, 400 are constructed from titanium, ceramic, or some other suitable biocompatible material. Those skilled in the art will also recognize that implants 100, 200, 300, 400 may be used to replace any tooth within a patient's mouth, and are not specific to any region in the mouth as long as the diameter of implants 100, 200, 300, 400 are varied and the angulations of top faces 112, 212, 312, 412 of each respective implant 100, 200, 300, 400 is varied according to the particular contours of the region.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A dental implant fixture comprising an elongated body extending along a longitudinal axis, wherein the body has a first end defining an attachment surface for mating with a dental crown and a second end that is configured to be inserted into bone, the first end of the dental implant fixture including:
   a first planar portion forming a planar mesiodistal face having a first angle extending obliquely with respect to the longitudinal axis and extending along a single plane between a mesial side and a distal side of the implant fixture; and
   a second planar portion forming a facial face having a second angle extending obliquely with respect to the longitudinal axis from a facial side partially toward a lingual side of the implant fixture,
   wherein the second planar portion intersects the first planar portion at an edge that is oriented obliquely with respect to the longitudinal axis.

2. The dental implant fixture according to claim 1, wherein the first end further comprises an external connection extending therefrom.

3. The dental implant fixture according to claim 1, wherein the first end comprises an internal connection extending thereinto.

4. The dental implant fixture according to claim 1, wherein at least a portion of the second end comprises a threaded connection.

5. The dental implant fixture according to claim 1, wherein the second angle extends obliquely relative to the first angle.

6. The dental implant fixture according to claim 1, wherein the first angle comprises a mesiodistal angle and the second angle comprises a facial angle.

7. The dental implant fixture according to claim 1, wherein the body comprises a polished exterior surface proximate to the attachment surface.

8. The dental implant fixture according to claim 1, wherein the body comprises a polished exterior portion extending from the first end toward the second end.

9. The dental implant fixture according to claim 8, further comprising a rough exterior portion extending from the polished exterior portion to the second end.

10. The dental implant fixture according to claim 1, further comprising a dental crown threadably coupled to the first end.

11. The dental implant fixture according to claim 10, further comprising a threaded coupling inserted through the dental crown and into the first end.

12. The dental implant fixture according to claim 11, further comprising a filler inserted into the dental crown and covering a top portion of the threaded coupling.

13. A method of installing a dental implant fixture into an oral cavity comprising:
   directing an implant fixture into the oral cavity, the implant fixture comprising an elongated body extending along a longitudinal axis, wherein the body has a first end defining an attachment surface for mating with a dental crown and a second end configured to be inserted into bone;
   orienting a first planar portion of the attachment surface to extend in a mesiodistal direction with respect to existing teeth within the oral cavity, the first planar portion forming a planar mesiodistal face having a first angle extending obliquely with respect to the longitudinal axis and extending along a single plane between a mesial side and a distal side of the implant fixture;
   orienting a second planar portion of the attachment surface to face the lips and/or cheek of the oral cavity, the second planar portion forming a facial face having a second angle extending obliquely with respect to the longitudinal axis from a facial side partially toward a lingual side of the implant fixture, wherein the second planar portion intersects the first planar portion at an edge that is oriented obliquely with respect to the longitudinal axis; and
   mating the dental crown to the attachment surface of the implant fixture.

14. The method of claim 13 further comprising attaching the dental crown to the attachment surface of the implant fixture, said attaching comprising: (i) positioning a screw through a passage formed in the dental crown, and (ii) threading the screw into an opening disposed in the implant fixture that extends from the first end and along the longitudinal axis of the implant fixture.

15. The method of claim 14 further comprising inserting a filler into the passage formed in the dental crown so that the filler covers a head of the screw.

* * * * *

UNITED STATES PATENT AND TRADEMARK OFFICE
CERTIFICATE OF CORRECTION

PATENT NO. : 7,618,258 B2  
APPLICATION NO. : 11/282929  
DATED : November 17, 2009  
INVENTOR(S) : Dumitru Gogarnoiu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Nineteenth Day of October, 2010

David J. Kappos
*Director of the United States Patent and Trademark Office*